United States Patent [19]
Gilman

[11] Patent Number: 5,453,431
[45] Date of Patent: Sep. 26, 1995

[54] USE OF HYDROXYCHLOROQUINE FOR TREATMENT OF GRAFT-VERSUS-HOST DISEASE

[76] Inventor: Andrew L. Gilman, 3419 Reservoir Rd., NW., Washington, D.C. 20007

[21] Appl. No.: 146,356

[22] Filed: Oct. 29, 1993

[51] Int. Cl.⁶ .................................................. A61K 31/47
[52] U.S. Cl. ........................................ 514/313; 514/885
[58] Field of Search ................................. 514/313, 885

[56] References Cited

U.S. PATENT DOCUMENTS

| | | | |
|---|---|---|---|
| 2,546,658 | 3/1951 | Surrey | 260/286 |
| 4,419,352 | 12/1983 | Cox et al. | 546/89 X |
| 4,657,763 | 4/1987 | Finkelstein | 424/131 |
| 4,968,702 | 11/1990 | Poletto et al. | 514/313 |
| 5,242,687 | 9/1993 | Tykoinski et al. | 514/885 X |
| 5,262,424 | 11/1993 | Kao | 514/291 |
| 5,314,894 | 5/1994 | Seder et al. | 514/313 |
| 5,330,993 | 7/1994 | Armistead et al. | 514/330 |

*Primary Examiner*—Richard L. Raymond
*Attorney, Agent, or Firm*—Liza D. Hohenschutz; William J. Davis

[57] ABSTRACT

The present invention provides methods of treating graft-versus-host disease comprising administering to a patient having graft-versus-host disease an effective mount of hydroxychloroquine. The present invention aim provides a method of suppressing alloreactivity arising from reactions of donor T lymphocytes against recipient cells comprising administering to said cells an amount of hydroxychloroquine effective to suppress such alloreaetivity.

7 Claims, No Drawings tion and cytokine production resulting from alloreactivity, such as when donor bone marrow cells are transplanted into a recipient patient and react with the recipient individual's cells.

USE OF HYDROXYCHLOROQUINE FOR TREATMENT OF GRAFT-VERSUS-HOST DISEASE

FIELD OF THE INVENTION

The present invention relates to the field of treatments for graft-versus-host disease arising after transplantation of donor cells into a host. More particularly, the present invention relates to the use of hydroxychloroquine (2-[[4-[(7-chloro-4-quinolinyl)amino] pentyl]ethylamino]ethanol) for prevention and treatment of graft-versus-host disease.

BACKGROUND OF THE INVENTION

Whenever a patient with a profound immunodeficiency (primary, secondary, or iatrogenic) receives a graft of an organ rich in immunocompetent cells there is a considerable risk that a graft-versus-host reaction may develop. Such reactions are a significant problem in infants and children with primary immunodeficiencies on whom a bone marrow transplant is performed with the goal of reconstituting the immune system and in patients receiving a bone marrow transplant for the treatment of malignancy. Many patients receiving bone marrow transplants have received cytotoxic/immunosuppressive therapy and their immune system is completely or partially destroyed.

Allogeneic bone marrow transplants have been demonstrated to be of use in curing patients with hematological malignancies, aplastic anemia, and congenital immunodeficiency and metabolic diseases. Allogeneic bone marrow transplant involves the transfer of hematopoeitic and immunocompetent lymphoid elements from a donor into a recipient. The transfer is preceded by bone marrow ablative high-dose chemotherapy and radiation therapy aimed at eliminating the recipient's underlying malignancy and/or at suppressing the recipient's immune system (to prevent rejection of the foreign tissue). The recipient's bone marrow is then repopulated with donor stem cells. These donor cells also lead to reconstitution of the recipient's immune system.

The major complication of allogeneic bone marrow transplant has been the development of graft-versus-host disease (GVHD) mediated by donor T lymphocytes that attack tissues (mainly skin, gastrointestinal tract, and liver) of the recipient. Graft-versus-host disease can be manifested both acutely (within weeks of transplant) or chronically (lasting from months to years after bone marrow transplant and usually following acute graft-versus-host disease). Acute graft-versus-host disease is manifested by a maculopapular, erythematous rash, diarrhea, and hepatitis. Immune reconstitution is also impaired resulting in a prolonged severe immunosuppression. Chronic graft-versus-host disease resembles autoimmune disorders in the development of sclerotic and mucous membrane and skin changes, pulmonary fibrosis and immune-mediated hemolytic anemia and thrombocytopenia. T cell depletion techniques, drugs such as prednisone and cyclosporine A (CSA) and toxin-linked antibodies directed against T cells have been used with moderate success to prevent or ameliorate acute graft-versus-host disease. Unfortunately, treatment of chronic graft-versus-host disease which occurs in thirty to sixty per cent of patients has been much less successful. Also, the treatments of acute graft-versus-host disease discussed above are limited by toxicities, including hypertension, decreased renal function and most importantly, an increase in the ability of the recipient's immune system to reject the bone marrow graft and an increased incidence of leukemic relapse (associated with T cell depletion).

Once a graft-versus-host reaction is initiated, its control may be extremely difficult. Cyclosporine A administration has met with some success, both in therapy and in prophylaxis. Patients treated with cyclosporine A have less frequent and less severe episodes of graft-versus-host disease. However, cyclosporine A is nephrotoxic, causes hypertension and has been associated with accelerated atherosclerosis particularly in heart transplants. The most efficient approach to the prevention of graft-versus-host disease is to eliminate T cells from the graft. The major problem with this approach is that the transplant of T-cell depleted bone marrow into immunosuppressed adults results in a persistently profound state of severe immunodeficiency with increased incidence of opportunitic infections and also in a higher incidence of leukemic relapse.

U.S. Pat. No. 4,657,763 discloses the use of combinations of gold salts and hydroxychloroquine for treating autoimmune disease such as rheumatoid arthritis. This patent also discloses that the combination of drugs can be used to prevent rejection of organ transplants such as heart and kidney transplants. However, there is no suggestion that hydroxychloroquine is itself effective for this purpose in the absence of gold salts.

In view of the drawbacks associated with known methods of reducing or preventing graft-versus-host disease there exists a real need for methods of treating this disease that can be administered for long periods of time without severe side effects and that reduce the need for T cell depletion of the donor bone marrow cells.

SUMMARY OF THE INVENTION

The present invention provides method of treating graft-versus-host disease in patients who have undergone bone marrow transplant. The method of the invention comprises administering to a mammal having graft-versus-host disease and in need of such treatment an effective mount of hydroxychloroquine (2-[[4-[(7-chloro-4-quinolinyl)amino] pentyl]ethylamino]ethanol).

Another aspect of the invention provides a method of suppressing alloreactivity arising from reaction of donor T lymphocytes against recipient cells comprising administering to the donor T lymphocytes and recipient cells an amount of hydroxychloroquine effective to suppress such alloreactivity. Applicant has found that hydroxychloroquine can suppress the cytotoxicity, proliferation and cytokine production resulting from allorecognition such as when donor bone marrow cells are transplanted into a recipient patient and react with the recipient individual's cells.

Hydroxychloroquine has been shown to be safe when administered to humans and other animals. Hydroxychloroquine avoids the nephrotoxicity and other side effects associated with cyclosporine A, and avoids the problems of severe immunodepression associated with depletion of T cells in the bone marrow before transplantation.

The present invention is more particularly pointed out in the appended claims and is described in its preferred embodiments in the following description.

DETAILED DESCRIPTION OF THE INVENTION

Hydroxychloroquine has been used for more than thirty years for the treatment of rheumatoid arthritis and other autoimmune diseases. Applicant has now discovered that hydroxychloroquine can suppress the cytotoxicity, proliferation and cytokine production resulting from allorecognition and may be useful for treating graft-versus-host disease in connection with bone marrow transplants and may also useful for treating rejection of transplanted organs and other tissues.

Allogeneic bone marrow transplant involves the transfer of hematopoeitic and immunocompetent lymphoid elements from a donor into a recipient. The major complication of allogeneic bone marrow transplant has been the development of graft-versus-host disease. Graft-versus-host disease in bone marrow transplants is associated with alloreactivity of donor T lymphocytes against recipient cells. Alloreactivity requires several steps. The first is recognition of foreign tissue antigens. Based on the knowledge that T cells recognize as antigens small peptides in the context of major histocompatibility antigens (human leukocyte antigen or HLA in the human system) several mechanisms of alloreaction have been proposed.

At the present time it is believed that T cells recognize foreign antigens as (1) intact foreign HLA molecule with an endogenous peptide that resembles a self HLA molecule with a previously seen foreign (i.e. viral) peptide (known as molecular mimicry, (2) a foreign HLA molecule-derived peptide in the context of a self B molecule, and (3) an intact empty foreign HLA molecule that again resembles a self HLA molecule with a foreign peptide. Required steps in the process include (1) the presence of foreign HLA molecules on the surface of foreign cells, (2) the ingestion of foreign HLA molecules by antigen-presenting cells (APC), the catabolism of these HLA molecules, and finally the presentation of peptides derived from these HLA molecules in the context of self HLA molecules and (3) the processing and presentation of endogenously produced peptides in the context of self and foreign HLA molecules. The processing of foreign antigens and of self (or virally encoded) endogenous peptides takes place via different mechanisms. Exogenous proteins are endocytosed by APC and then transported to acid lysosomes where acid hydrolases cleave the protein into peptide antigens. These peptides are then loaded into HLA class II molecules that were previously occupied by invariant chains, and transported to the cell's surface. These exogenous peptides in the context of class II HLA molecules are recognized by CD4+lymphocytes. Endogenous peptides produced by antigen presenting cells are believed to associate with class I HLA molecules in the Golgi apparatus. These endogenous peptides in the context of class I HLA molecules are recognized by CD8+T lymphocytes. Alloreactivity also requires elaboration of costimulatory signals by the antigen-presenting cells, including the secretion of interleukin-1(IL-1), Interleukin-6 (IL-6) and TNF-a. Finally, the T cells themselves participate by secreting the T cell growth factor, interleukin-2 (IL-2) and other factors involved in T cell regulation including interleukin-4 (IL-4) and 2-interferon (2-INF).

Applicant has found that hydroxychloroquine exerts a dose-dependent suppression of alloreactivity generated by mixed lymphocyte culture. This suppression is apparent for both cytotoxicity and proliferation. The effect of cytotoxicity is not merely due to decreased proliferation since the viable cell yield at the end of the mixed lymphocyte culture is similar regardless of the hydroxychloroquine concentration present and since the number of effector cells in the cytotoxicity assays is adjusted to be the same at all hydroxychloroquine concentrations. Immunophenotyping of the effector cells resulting from mixed lymphocyte culture revealed comparable numbers of CD4+ and CD8+ cells at all concentrations demonstrating that certain subsets were not deleted by hydroxychloroquine.

Hydroxychloroquine does not solely mediate its effect through antigen presentation and other early events in mixed lymphocyte culture since addition of hydroxychloroquine as late as 24–120 hours after the initiation of the mixed lymphocyte culture still has an effect on cytotoxicity (although usually the efficiency diminishes the later the hydroxychloroquine is added). The effect of hydroxychloroquine is reversed by washing the effector cells prior to secondary mixed lymphocyte culture making tolerance an unlikely mechanism. Since hydroxychloroquine interferes with receptor recycling and may alter HLA antigen loading and presentation, the incubation of target cells with hydroxychloroquine was undertaken to determine whether this would decrease lysis by effector cells that had not been exposed to hydroxyehloroquine. Hydroxyehloroquine had no effect in this situation. Flow cytometry has not demonstrated a decrease in HLA antigen expression at any hydroxychloroquine concentration.

Finally, it has been found by Applicant that hydroxychloroquine decreases TNF-a. and IL-6 production resulting from allorecognition. In light of hydroxychloroquine's ability to suppress the cytotoxicity, proliferation and cytokine production resulting from allorecognition, hydroxychloroquine should be useful in the prevention and treatment of graft-versus-host disease.

Hydroxychloroquine is 2-[[4-[(7-chloro-4-quinolinyl)amino]pentyl]ethylamino] ethanol (Surrey, U.S. Pat. No. 2,546,658, Mar. 27, 1951), and can be obtained as the sulfate salt from Sterling Drug, Inc., New York, N.Y. under the trade name Plaquenil®Sulfate. Other salts of hydroxychloroquine as well as the free base can be used in the methods of the invention. Suitable salts include the phosphate salt. This and other suitable salts as well as the free base are disclosed in U.S. Pat. No. 2, 546,658. In addition, it may also be possible to use chloroquine in the methods of the invention. However, the use of hydroxyehloroquine is much preferred due to the higher risk of adverse effects in the eye associated with chloroquine. Hydroxychloroquine can be formulated for oral or parenteral administration in solid, liquid or other appropriate dosage forms including tablets, capsules and solutions, using conventional pharmaceutically acceptable vehicles and techniques.

Hydroxychloroqulne may be administered to the patient in amounts effective to reduce or prevent graft-versus-host disease. In general, hydroxychloroquine may be administered to the patient in amounts of from about 600 milligrams per day to about 1,000 milligrams per day, preferably about 800 milligrams per day initially and the dose is adjusted downwards after good control of the disease is obtained to about 200 milligrams per day to about 600 milligrams per day, preferably about 400 milligrams day. The actual amount of hydroxychloroquine given to the patient will vary with such factors as the weight of the patent, and the organ function and physical condition of the patient. Hydroxyehloroquine may be initially administered to the patient for a period of at least about two to three months, or until the symptoms of graft-versus-host disease are reversed or stabilized. Hydroxychloroquine may also be administered to the patient for prolonged periods of time, if necessary, up to about three years after initiation of hydroxychloroquine therapy. When hydroxyehloroquine is given for long periods of time, it is recommended that the patient have regular eye examinations every three months. Hydroxychloroquine may be administered for treatment of chronic and acute graft-versus-host disease. Acute graft-versus-host disease appears within about one hundred days after transplantation of the donor bone marrow material. Chronic graft-versus-host disease appears about three months after transplantation of the donor bone marrow material. Reduction or prevention of graft-versus-host disease refers to reducing or preventing the effects of allorecognition as discussed and disclosed herein. Reduction or prevention of graft-versus-host disease also refers to reducing or preventing other symptoms of acute or chronic graft-versus-host disease.

The methods of the invention may be used to treat graft-versus-host disease in any species of mammal, including human patients, such as dogs, rats, mice, horses, etc. Generally, the donor bone marrow will be obtained from the same species as the recipient patient.

Hydroxychloroquine can be administered in conjunction with other treatments such as cyclosporine A, prednisone and or toxin-linked antibodies.

For suppression of alloreactivity, hydroxychloroquine is added to cells, in vivo or in vitro in amounts of from about 6 µM to about 25 µM, preferably about 12–13 µM. Applicant has found that hydroxychloroquine concentrations of 6.25 µM and 12.5 µM produced mean reductions in cytotoxicity of 30 and 64%, respectively, whereas a concentration of 25 µM completely abrogated (>90% reduction) cytotoxicity. A comparable dosage of hydroxychloroquine formulated for oral administration is about 800 milligrams per day which will provide a theoretical serum level of 10 µM. Other dosages of hydroxychloroquine can be formulated to provide suitable serum concentrations for suppression of alloreactivity in mammalian patients in vivo.

In view of the usefulness of hydroxychloroquine suppressing cytotoxicity, cell proliferation and cytokine production resulting from allorecognition, hydroxychloroquine may also be useful for treating rejection of transplanted organs, such as heart and kidney, as well as other tissues and organs. Hydroxychloroquine would be administered to patients having a transplanted organ or other tissue in amounts effective to reduce or prevent rejection of the organ or tissue by the recipient patient.

Experimental

1. Hydroxychloroquine suppresses the development of cytotoxicity resulting from allorecognition Healthy volunteer donors were used to obtain responder and stimulator cells. The generation of effector cells and cytotoxicity assays were performed according to the methods of Schendel et al. (1978) "Cell-mediated lympholysis: Examination of HLA genetic fine structure and complementation using cytotoxic T lymphocytes", Eur. J. Immunol. 8: 634. Mixed lymphocyte culture generates cytotoxicity secondary to allorecognition.

Peripheral blood mononuclear cells (PMBC) were isolated using Ficoll-Hypaque (Pharmacia, Piscataway, N.J.) density gradients. Mixed lymphocyte cultures (MLC) were set up using 10 million each of stimulator cells (irradiated with 2,500 rads) and responder cells in a total of 20 ml of complete medium. Complete medium consisted of RPMI-1640 medium, 10% (v/v) responder serum, penicillin, streptomycin, L-glutamine and tyrosine.

Effectors derived from the mixed lymphocyte cultures were washed once prior to cell toxicity assays, i.e. cell-mediated lympholysis (CML) assays. Target cells were prepared as specific targets (from the stimulator) and autologous targets (from the responder) either from phytohemagglutinin (PHA)-stimulated PMBC or from Epstein-Barr virus (EBV)-transformed B-lymphoblastoid cell lines. Targets were labeled with 100 µCi of $^{51}$Cr (DuPont, Wilmington, Del.) for a ninety minute incubation period. They were then washed twice and plated at a concentration of $3\times10^4$ cells per well of a 96-well microassay plate (Flow Laboratories, McLean, Va.). Effector cells are added at concentrations to provide effector:target cell ratios of 25:1 to 100:1 and a final volume of 0.2 ml/well. The assay was then incubated for four hours at 37° C. The plates were centrifuged briefly at 2,000 rpm and then 0.05 ml of supernatant was harvested. Twenty ml of scintillant for the Betaplate counter (PSA Laboratory, Loughborough, U.K.) was added to the supernatants and then the plates were counted on a Wallac beta counter (Wallac, Turku, Finland)/Specific lysis was calculated by the following formula:

$$\text{Specific lysis} = \frac{\text{test release(cpm)} - \text{spontaneous release(cpm)}}{\text{maximal release(cpm)} - \text{spontaneous release(cpm)}}$$

Maximal release was established by adding 0.1 ml of Triton-X (Bio-Rad, Richmond, Calif.) 5% instead of effectors and spontaneous release by adding 0.1 ml of media instead of effectors.

Hydroxychloroquine (Sanofi Winthrop Pharmaceuticals, New York, N.Y.) was used at final concentrations of 3.13 µM, 6.25 µM, 12.5 µM and 25 µM. Hydroxyehloroquine was added at the initiation of the mixed lymphocyte culture. This allowed hyclroxychloroquine to act on antigen catabolism, processing and presentation and on cytokine secretion by both antigen-processing cells and T cells. The controls were media controls.

Hydroxyehloroquine concentration of 6.25 and 12.5 µM produced mean reductions in cytotoxicity of 30 and 64%, respectively. A concentration of 25 µM completely abrogated (>90% reduction) cytotoxicity. Reduction of cytotoxicity was not on the basis of drug toxicity based on Trypan blue exclusion assessment of viability and cell yield at the end of the mixed lymphocyte culture. There appeared to be variation between individuals (or responder-stimulator pairs) as to the degree of suppression seen with the 12.5 µM concentration. A similar phenomenon has been described with the immunosuppressive agent cyclosporine A.

2. Treatment with hydroxychloroquine does not induce tolerance and does not irreversibly reduce T cell cytotoxic capability secondary to allorecognition.

Primary mixed lymphocyte cultures were performed as described in Example 1 with the same concentrations of hydroxychloroquine. On day 6 of incubation, some of the cells were tested in cytotoxicity assays as described in Example 1 to confirm that cytotoxicity had developed and that hydroxyehloroquine had the anticipated suppressive effect. Five million of the remaining effector cells were washed twice to remove the hydroxychlrorquine and then were restimulated with irradiated (2,500 rads) peripheral blood mononuelear cells from the same donor. These restimulated cells formed the secondary mixed lymphocyte culture (MLC). The effector cells from the secondary mixed lymphocyte culture were tested for cytotoxicity on Day 2–4 after restimulation using the cell-mediated lympholysis assay described in Example 1.

The effector cells were now capable of cytotoxicity, including those effectors that had originally been primed in the presence of the highest concentration of hydroxychloroquine. There appeared to be only a small reduction in the lysis mediated by the hydroxychloroquine-treated effectors. This data shows that hydroxychloroquine does not have a permanent effect (i.e. tolerance of suppression) on allorecognition once the drug is removed. The primary mixed lymphocyte culture had generated the anticipated effect of hydroxychloroquine on cytotoxicity.

3. Hydroxychloroquine suppresses proliferation in response to alloantigens and mitogens Proliferation in response to alloantigen was assessed by routine mixed lymphocyte culture. Briefly, PMBC were isolated with a Ficoll-Hypaque density gradient as described in Example 1. Fifty-thousand responders and fifty thousand irradiated stimulators (2,500 rads) were combined with concentrations of hydroxychlrorquine ranging from 3.25 µM to 25 µM at the initiation of the mixed lymphocyte culture. The final volume was 0.15 ml/well after 72 hours. Eighteen hours later, the cells were harvested onto a filter mat with a plate harvester Tomtec, Orange, Conn.) Ten ml of scintillant (FSA, U.K) was applied to the filter mat and which was then counted on a beta counter (Wallac, Finland).

PHA stimulation—The assay were performed as described hereinabove in Example 3, but phytohemagglutinin (PHA)(PHA-P, Difco, Detroit, Mich.) was used as a mitogen instead of stimulator cells to induce T cell proliferation. The responder cell numbers and the total volume were the same as the mixed lymphocyte culture proliferation assay.

The results of the mixed lymphocyte culture assay showed a dose-dependent decrease in proliferation with hydroxychloroquine. The hydroxychloroquine concentration of 12.5 µM produced a reduction of 33% and 25 µM produced a mean reduction of 75%. The degree of reduction of proliferation was strikingly lower than the reduction in cytotoxicity. This suggests that the hydroxychloroquine effect in cytotoxicity is not solely secondary to a decreased proliferation of effector cells. The effect of hydroxychloroquine on mitogen-induced proliferation was also assessed as a means of circumventing the need for antigen processing. Phytohemagglutinin (PHA) stimulation of T cell proliferation was reduced 41% at 12.5 µM hydroxychloroquine and 72% at 25 µM hydroxychloroquine. The similar result seen with PHA and with mixed lymphocyte culture suggests that hydroxychloroquine's effect on proliferation secondary to allorecognition is not primarily through antigen presentation.

4. Effect of combination of hydroxychloroquine and cyclosporine A

Hydroxychloroquine was tested to see if its effect on proliferation due to allorecognition would be additive or synergistic with cyclosporine A in vitro The assay disclosed in Example 3 (mixed lymphocyte culture proliferation assay ) was repeated using varying concentrations (0.1 ng, 1 ng, 10 ng and 100 ng/ml) of cyclosporine A (CSA) in addition to hydroxychloroquine. The responder cell numbers and the total volume were the same as the mixed lymphocyte culture proliferation assay.

Results suggest that hydroxychloroquine is at least additive and often synergistic with cyclosporine A for the reduction of proliferation. Even if hydroxychloroquine and cyclosporine A are only additive, this would still be of clinical importance since the use of both drugs together may allow reduction in the doses of both and thereby decrease their nonoverlapping toxicities.

5. Hydroxychloroquine does not influence the subsets of responder T cells during mixed lymphocyte cultures.

Mixed lymphocyte cultures were prepared as described in Example 1. The range of hydroxychloroquine concentrations used was 3.25 µM - 25 µM. Assay were performed on either day 6 after primary mixed lymphocyte culture or day 3 after secondary mixed lymphocyte culture as described in Example 2. For studies performed in Day 3 after secondary mixed lymphocyte culture, the cells were incubated with hydmxychloroquine for the primary mixed lymphocyte culture, but then were washed prior restimulation to the on Day 6. The cells were stained with fluorescein or phycoerythin-conjugated antibodies (Becton-Dickinson, San Jose, Calif.) against the following antigens: CD3 (pan T cell), CD4 (helper/inducer T cell), CD8 (cytotoxic/suppressor cell) CD20 (B cell), CD56 (natural killer cell). Indirect staining of the cells was also done by incubating them with the unconjugated antibody specific for CD25 (high-affinity interleukin-2 receptor) followed by incubation with fluorescein-conjugated goat anti-mouse antibody. Fluorescence activated cells sorting (FACS) analysis was then used to assess the phenotype of the responding cells during mixed lymphocyte culture.

The results of this experiment showed that there are minimal decreases in the CD4+ (helper/inducer) and CDS+ (cytotoxic/suppressor) T cell population and usually only at the highest concentration of hydroxychloroquine (25 µM). This decrease, although small, is most apparent in CD4+ cells at 72 hours after the mixed lymphocyte culture is initiated. Interestingly, studies of patients with rheumatoid arthritis being treated with hydroxychloroquine have demonstrated decreased numbers of CD4+cells. This data might reflect secondary changes as a result of decreased cytokine production or antigen presentation. A direct cytotoxic effect on CD4+cells is unlikely since numbers are comparable on Day 6 of the mixed lymphocyte culture. Since effector numbers are adjusted to be the same at the time of cytotoxicity assays and since the percentages of T cell subsets are similar, the differences in cytotoxicity seen with hydroxychloroquine treatment cannot solely be accounted for by depletion of a subset of T cells or by decreased proliferation. However, this does not rule out that specific alloreactive T cell clones are not being expanded or that subsets of the CD4+or CD8+populations are being depleted. Most concentrations of hydroxychloroquine do not affect the phenotype of the responding cells. CD25 expression was not decreased at concentrations of hydroxychloroquine sufficient to down regulate proliferation and toxicity resulting form alloreactivity.

6. Hydroxychloroquine does not exclusively function at the time of T cell activation.

Time course experiments in which hydroxychloroquine was added either at the initiation of the mixed lymphocyte culture or 24 to 120 hours later were performed to see if hydroxychloroquine was acting on early events such as T cell activation and antigen processing. Mixed lymphocyte culture was performed according to the method described in Example 1 except that for some portions of the cells hydroxychloroquine was added at 24 to 120 hours after the initiation of the mixed lymphocyte culture. Cytotoxicity was assessed on Day 6 according to the cytotoxicity assay described in Example 1.

The results demonstrate that there is usually no difference in the effect on cytotoxicity whether hydroxychloroquine is added at the initiation of the mixed lymphocyte culture or at 24 hours at 0.0125 µM and as late as 48 hours at 0.025 µM. Addition of hydroxychloroquine at 72 hours or later usually resulted in a decreased reduction of cytotoxicity. This decrease when added at 120 hours was present in 78% of experiments at 0.0125 µM and 60% of experiments at 0.025 µM. Interestingly, there was still 46% decrease in cytotoxicity at 0.0125 µM and 68% decrease at 0.025 µM (compared to 78% and 94%, respectively, when hydroxychloroquine was added at the initiation of the mixed lymphocyte culture). Although an effect on early events is likely in light of the decrease in inhibition of cytotoxicity with the late addition of hydroxychloroquine, the fact that a significant degree of inhibition remains suggests that effects on later events or mediators of cytotoxicity are also important.

7. Effect of hydroxychloroquine added only at the time of the cell-mediated lysis assay Mixed lymphocyte culture was performed as described in Example 1 except that hydroxychloroquine was omitted from the culture and added in the same concentrations at the time of the cytotoxicity assay that was performed as described in Example 1.

Addition of hydroxychloroquine only at the time of the cytotoxicity assay resulted in suppression of target cell lysis. The effect when hydroxychloroquine was added to the cytotoxicity assay only was less than when hydroxychloroquine was present for the entire mixed lymphocyte culture at the 25 µM concentration of hydroxychloroquine but was comparable for other concentrations. Again, this suggests that hydroxychloroquine has an effect on late events (i.e. cytokine secretion) or lytic mechanisms.

8. HLA antigen expression

The effect of hydroxychloroquine concentration of 3.25–100 µM for different incubation times (two vs. 24 hours) on HLA antigen expression was examined. The higher concentrations were used for the short incubation periods based on data regarding the accumulation of hydroxychloroquine in PMBC. HLA antigen expression was detected by indirect immunofluorescence using the w 6/32 antibody (specific for HLA Class I antigens) and the L243 antibody (specific for HLA Class II antigens) (both antibodies were obtained from Hazelton, Lenexa, Kans.) with the subsequent use of goat anti-mouse fluorescein isothiocyanate (FITC)-conjugated antibody. PMBC were isolated with Ficoll-Hypaque density gradient. They were then incubated with the antibodies w 6/32 and L243 for 30 minutes at 4° C. Thereafter, they were washed twice and then incubated with a fluorescein-conjugated goat anti-mouse antibody (Becton-Dickinson, San Jose, Calif.) for 30 minutes at 4° C. The cells were washed and then fixed with formalin. Goat anti-mouse antibody alone was use as a negative control. Finally, the samples were assessed by FACS analysis (FACSCAN, Becton-Dickinson) for their Class I and II expression.

Flow cytometry revealed no evidence of down regulation of Class I or II HLA antigen expression. This data suggests that altered HLA antigen expression on the stimulator cells is not responsible for the decrease in alloreactivity.

9. Influence of hydroxychloroquine on cytokine production

Cytokine release in mixed lymphocyte culture performed as described in Example 1 with hydroxychloroquine at concentrations of 3.25 µM - 25 µM was assessed by testing supernatants with commercially-available cytokine ELISA kits (Biosource, Camarillo, Calif.). The ELISA assays were performed according to the manufacturer's instructions. Absorbance was measured at $OD_{450}$. Supernatants were collected on Days 0 (2 hours after cell culture initiation), 1, 3, and 6 of mixed lymphocyte culture. The supernatants were frozen at –20° C. immediately after they were harvested. They were then tested in batches when sufficient numbers of samples were available. The cytokines tested included tumor necrosis factor-$\alpha$(TNF-$\alpha$) and interleukin-6 (IL-6).

Hydroxychloroquine showed a suppressive effect on the production of TNF-$\alpha$ and IL-6 with a dose-response relationship. There was not a good correlation between the decrease in either cytokine and cytotoxicity. 10. Hydroxychloroquine effect on bone marrow in vitro The effect of hydroxychloroquine on the clonogenic potential of mice and human bone marrow was assessed by placing $1\times10^5$ bone marrow mononuclear cells in 1 ml of semisolid medium containing methylcellulose (methylcellulose ready mix without growth factors #HCC 3230, Terry Fox, Vancouver, Canada), supplemented with erythropoeitin (2 unit/ml, Ortho Biotech, Somerset, N.J.), recombinant murine granulocyte/macrophage colony stimulating factor (GM-CSF) (Promega, Madison, Wis.) or human recombinant GM-CSF (Immunex, Seattle, Wash.) 0.5 ng/ml and hydroxychloroquine at concentrations of 3.25 µN - 25 µM. A control culture without hydroxychloroquine was also plated. One ml cultures in duplicate were plated in 35 mm Petri dishes. On day 7, the total number of colonies (CFU-C) was determined using an inverted microscope.

Bone marrow clonogenic assays demonstrated no effect on the growth of murine bone marrow and a small effect on human bone marrow.

I claim:

1. A method of treating graft-versus-host disease consisting essentially of administering to a mammal having graft-versus-host disease after bone marrow transplant and in need of such treatment an effective amount of hydroxychloroquine.

2. The method of claim 1 wherein said hydroxychoroquine is administered to said mammal in amounts of from about 600 to about 1,000 milligrams per day.

3. The method of claim 2 wherein said hydroxyehloroquine is administered to said mammal in amounts of about 800 milligrams per day.

4. The method of claim 1 wherein said hydroxychloroquine is administered to said mammal in amounts of from about 200 to about 600 milligrams per day.

5. The method of claim 4 where in said hydroxychloroquine is administered to said mammal in mounts of about 400 milligrams per day.

6. A method of suppressing alloreactivity in a recipient patient having bone marrow cells transplant and in need of suppression of alloreactivity arising from reaction of donor T lymphocytes against recipient cells consisting essentially of administering or adding to said donor T lymphocytes and said recipient cells an amount of hydroxychloroquine effective to suppress such alloreactivity.

7. The method of claim 6 wherein said effective amount of hydroychloroquine is from about 6 to about 25 µM hydroxychloroquine.

* * * * *